(12) United States Patent
Mishelevich et al.

(10) Patent No.: US 8,723,628 B2
(45) Date of Patent: May 13, 2014

(54) SHAPED COILS FOR TRANSCRANIAL MAGNETIC STIMULATION

(75) Inventors: David J. Mishelevich, Playa del Rey, CA (US); M. Bret Schneider, Portola Valley, CA (US)

(73) Assignee: Cervel Neurotech, Inc., Redwood City, CA (US)

( * ) Notice: Subject to any disclaimer, the term of this patent is extended or adjusted under 35 U.S.C. 154(b) by 19 days.

(21) Appl. No.: 13/141,100

(22) PCT Filed: Jan. 7, 2010

(86) PCT No.: PCT/US2010/020324
§ 371 (c)(1),
(2), (4) Date: Aug. 1, 2011

(87) PCT Pub. No.: WO2010/080879
PCT Pub. Date: Jul. 15, 2010

(65) Prior Publication Data
US 2011/0273251 A1    Nov. 10, 2011

Related U.S. Application Data

(60) Provisional application No. 61/143,103, filed on Jan. 7, 2009.

(51) Int. Cl.
*H01F 5/00* (2006.01)
*A61N 1/00* (2006.01)
(52) U.S. Cl.
USPC .............. 335/299; 335/216; 335/284; 600/13
(58) Field of Classification Search
USPC .......................... 335/216, 284, 299
See application file for complete search history.

(56) References Cited

U.S. PATENT DOCUMENTS

| 3,799,164 A | 3/1974 | Rollins |
| 4,134,395 A | 1/1979 | Davis |

(Continued)

FOREIGN PATENT DOCUMENTS

| DE | 10242542 A1 | 4/2004 |
| EP | 0501048 A1 | 9/1992 |

(Continued)

OTHER PUBLICATIONS

Aleman et al.; Efficacy of slow repetitive transcranial magnetic stimulation in the treatment of resistant auditory hallucinations in schizophrenia: a meta-analysis; J Clin Psychiatry; 68(3):416-21; Mar. 2007.

(Continued)

*Primary Examiner* — Mohamad Musleh
(74) *Attorney, Agent, or Firm* — Shay Glenn LLP

(57) ABSTRACT

Described herein are shaped coil TMS electromagnets formed by two bent magnetic coil loops joined at a vertex having an angle between the outer coil regions of the coils that is typically less than 120 degrees (e.g., between about 45 and about 70 degrees, 60 degrees, etc.). The vertex region shaped to optimize the magnetic field projected from the TMS electromagnet. For example, the vertex region may be horizontal or vertical. In some variations the vertex region is formed by re-arranging the conductive windings forming the two coils so that they are no longer arranged in the same columnar structure that they are in the other portions of the bent magnetic coil loops. These TMS electromagnets may be well suited for use in deep-brain Transcranial Magnetic Stimulation.

18 Claims, 5 Drawing Sheets

(56) References Cited

U.S. PATENT DOCUMENTS

| | | | |
|---|---|---|---|
| 4,889,526 A | 12/1989 | Rauscher et al. | |
| 5,207,223 A | 5/1993 | Adler | |
| 5,267,938 A | 12/1993 | Konotchick | |
| 5,427,097 A | 6/1995 | Depp | |
| 5,441,495 A | 8/1995 | Liboff et al. | |
| 5,531,227 A | 7/1996 | Schneider | |
| 5,707,334 A | 1/1998 | Young | |
| 5,738,625 A | 4/1998 | Gluck | |
| 5,766,124 A | 6/1998 | Polson | |
| 5,891,034 A | 4/1999 | Bucholz | |
| 6,042,531 A | 3/2000 | Holcomb | |
| 6,132,361 A | 10/2000 | Epstein et al. | |
| 6,132,631 A | 10/2000 | Nallan et al. | |
| 6,149,577 A | 11/2000 | Bouldin et al. | |
| 6,179,770 B1 | 1/2001 | Mould | |
| 6,179,771 B1 | 1/2001 | Mueller | |
| 6,198,958 B1 | 3/2001 | Ives et al. | |
| 6,236,875 B1 | 5/2001 | Bucholz et al. | |
| 6,266,556 B1 | 7/2001 | Ives et al. | |
| 6,351,573 B1 | 2/2002 | Schneider | |
| 6,356,781 B1 | 3/2002 | Lee et al. | |
| 6,425,852 B1 | 7/2002 | Epstein et al. | |
| 6,447,440 B1* | 9/2002 | Markoll | 600/13 |
| 6,461,289 B1 | 10/2002 | Muntermann | |
| 6,488,617 B1 | 12/2002 | Katz | |
| 6,507,751 B2 | 1/2003 | Blume et al. | |
| 6,537,197 B1 | 3/2003 | Ruohonen et al. | |
| 6,571,123 B2 | 5/2003 | Ives et al. | |
| 6,572,528 B2 | 6/2003 | Rohan et al. | |
| 6,663,556 B2 | 12/2003 | Barker | |
| 6,818,669 B2 | 11/2004 | Moskowitz et al. | |
| 6,849,040 B2 | 2/2005 | Ruohonen et al. | |
| 6,858,000 B1 | 2/2005 | Naraikin et al. | |
| 6,972,097 B2 | 12/2005 | Yoshida et al. | |
| 7,023,311 B2* | 4/2006 | Baldwin et al. | 336/5 |
| 7,087,008 B2 | 8/2006 | Fox et al. | |
| 7,088,210 B2 | 8/2006 | Day et al. | |
| 7,104,947 B2 | 9/2006 | Riehl | |
| 7,141,028 B2 | 11/2006 | McNew | |
| 7,153,256 B2 | 12/2006 | Riehl et al. | |
| 7,155,284 B1 | 12/2006 | Whitehurst et al. | |
| 7,236,830 B2 | 6/2007 | Gliner | |
| 7,239,910 B2 | 7/2007 | Tanner | |
| 7,367,935 B2 | 5/2008 | Mechlenburg et al. | |
| 7,367,936 B2 | 5/2008 | Myers et al. | |
| 7,396,326 B2 | 7/2008 | Ghiron et al. | |
| 7,483,747 B2 | 1/2009 | Gliner et al. | |
| 7,520,848 B2 | 4/2009 | Schneider et al. | |
| 7,771,341 B2 | 8/2010 | Rogers | |
| 7,856,264 B2 | 12/2010 | Firlik et al. | |
| 7,904,134 B2 | 3/2011 | McIntyre et al. | |
| 8,052,591 B2 | 11/2011 | Mishelevich | |
| 8,265,910 B2* | 9/2012 | Mishelevich et al. | 703/2 |
| 2002/0022777 A1 | 2/2002 | Crieghton et al. | |
| 2002/0097125 A1 | 7/2002 | Davey | |
| 2003/0004392 A1 | 1/2003 | Tanner et al. | |
| 2003/0028072 A1 | 2/2003 | Fischell et al. | |
| 2003/0065243 A1 | 4/2003 | Tanner | |
| 2003/0204135 A1 | 10/2003 | Bystritsky | |
| 2004/0010177 A1 | 1/2004 | Rohan et al. | |
| 2004/0077921 A1 | 4/2004 | Becker et al. | |
| 2004/0078056 A1* | 4/2004 | Zangen et al. | 607/2 |
| 2004/0193000 A1 | 9/2004 | Riehl | |
| 2004/0193002 A1 | 9/2004 | Tanner et al. | |
| 2005/0033154 A1 | 2/2005 | deCharms | |
| 2005/0038313 A1 | 2/2005 | Ardizzone | |
| 2005/0046532 A1* | 3/2005 | Dodd | 335/299 |
| 2005/0107655 A1 | 5/2005 | Holzner | |
| 2005/0113630 A1 | 5/2005 | Fox et al. | |
| 2005/0124848 A1 | 6/2005 | Holzner | |
| 2005/0148808 A1 | 7/2005 | Cameron et al. | |
| 2005/0154426 A1 | 7/2005 | Boveja et al. | |
| 2005/0222625 A1 | 10/2005 | Laniado et al. | |
| 2005/0234286 A1 | 10/2005 | Riehl et al. | |
| 2005/0256539 A1 | 11/2005 | George et al. | |
| 2006/0058853 A1 | 3/2006 | Bentwich | |
| 2006/0094924 A1 | 5/2006 | Riehl et al. | |
| 2006/0106430 A1 | 5/2006 | Fowler et al. | |
| 2006/0122454 A1 | 6/2006 | Riehl et al. | |
| 2006/0122496 A1 | 6/2006 | George et al. | |
| 2006/0149337 A1 | 7/2006 | John | |
| 2006/0173274 A1 | 8/2006 | George et al. | |
| 2006/0189866 A1 | 8/2006 | Thomas et al. | |
| 2006/0199992 A1* | 9/2006 | Eisenberg et al. | 600/14 |
| 2006/0218790 A1 | 10/2006 | Day et al. | |
| 2006/0287566 A1 | 12/2006 | Zangen et al. | |
| 2007/0027353 A1* | 2/2007 | Ghiron et al. | 600/9 |
| 2007/0027504 A1 | 2/2007 | Barrett et al. | |
| 2007/0083074 A1 | 4/2007 | Sotiriou | |
| 2007/0100392 A1 | 5/2007 | Maschino et al. | |
| 2007/0100398 A1 | 5/2007 | Sloan | |
| 2007/0242406 A1* | 10/2007 | Annis et al. | 361/147 |
| 2007/0260107 A1* | 11/2007 | Mishelevich et al. | 600/14 |
| 2007/0265489 A1 | 11/2007 | Fowler et al. | |
| 2007/0293916 A1 | 12/2007 | Peterchev | |
| 2008/0033297 A1 | 2/2008 | Sliwa | |
| 2008/0058582 A1 | 3/2008 | Aho et al. | |
| 2008/0064950 A1 | 3/2008 | Ruohonen et al. | |
| 2008/0123922 A1 | 5/2008 | Gielen et al. | |
| 2008/0161636 A1 | 7/2008 | Hurme et al. | |
| 2008/0306326 A1 | 12/2008 | Epstein | |
| 2009/0018384 A1 | 1/2009 | Boyden et al. | |
| 2009/0024021 A1 | 1/2009 | George et al. | |
| 2009/0099405 A1 | 4/2009 | Schneider et al. | |
| 2009/0099623 A1 | 4/2009 | Bentwich | |
| 2009/0112133 A1 | 4/2009 | Deisseroth et al. | |
| 2009/0112277 A1 | 4/2009 | Wingeier et al. | |
| 2009/0114849 A1 | 5/2009 | Schneider et al. | |
| 2009/0124848 A1 | 5/2009 | Miazga | |
| 2009/0156884 A1* | 6/2009 | Schneider et al. | 600/14 |
| 2009/0187062 A1 | 7/2009 | Saitoh | |
| 2009/0189470 A1 | 7/2009 | McClellan | |
| 2009/0227830 A1 | 9/2009 | Pillutla et al. | |
| 2009/0234243 A1 | 9/2009 | Schneider et al. | |
| 2010/0004500 A1 | 1/2010 | Gliner et al. | |
| 2010/0185042 A1* | 7/2010 | Schneider et al. | 600/13 |
| 2010/0256436 A1 | 10/2010 | Partsch et al. | |
| 2010/0256438 A1* | 10/2010 | Mishelevich et al. | 600/13 |
| 2010/0256439 A1 | 10/2010 | Schneider et al. | |
| 2010/0298623 A1 | 11/2010 | Mishelevich et al. | |
| 2010/0331602 A1 | 12/2010 | Mishelevich et al. | |
| 2011/0004450 A1* | 1/2011 | Mishelevich et al. | 703/2 |
| 2011/0082326 A1 | 4/2011 | Mishelevich et al. | |
| 2012/0016177 A1 | 1/2012 | Mishelevich et al. | |
| 2012/0310035 A1 | 12/2012 | Schneider et al. | |
| 2013/0096363 A1 | 4/2013 | Schneider et al. | |

FOREIGN PATENT DOCUMENTS

| | | |
|---|---|---|
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |

(56) References Cited

FOREIGN PATENT DOCUMENTS

| WO | WO 2007/050592 A2 | 5/2007 |
|---|---|---|
| WO | WO 2007/130308 A2 | 11/2007 |
| WO | WO 2009/042863 A1 | 4/2009 |

OTHER PUBLICATIONS

Alonso et al.; Right prefrontal repetitive transcranial magnetic stimulation in obsessive-compulsive disorder: a double-blind, placebo-controlled study; Am J Psychiatry; 158(7):1143-5; Jul. 2001.

Antal et al.; Transcranial Direct Current Stimulation Over Somatosensory Cortex Decreases Experimentally Induced Acute Pain Perception; Clin J Pain; vol. 24, No. 1; pp. 56-63; Jan. 2008.

Bikson et al.; Transcranial Direct Current Stimulation for Major Depression: A General System for Quantifying Transcranial Electrotherapy Dosage; Current Treatment Options in Neurology; 10(5):377-385; Sep. 2008.

Boggioa et al.; A randomized, double-blind clinical trial on the efficacy of cortical direct current stimulation for the treatment of major depression; International Journal of Neuropsychopharmacology; 11(2): 249-254; Mar. 2008.

Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar. 2004.

Fecteau et al.; Diminishing risk-taking behavior by modulating activity in the prefrontal cortex: a direct current stimulation study; J Neurosci.; 27(46):12500-5; Nov. 14, 2007.

Fitzgerald et al.; Transcranial magnetic stimulation in the treatment of depression: a double-blind, placebo-controlled trial; Arch Gen Psychiatry; 60(10):1002-8; Oct. 2003.

Fregni et al.; Anodal transcranial direct current stimulation of prefrontal cortex enhances working memory; Exp Brain Res.; 166(1); pp. 23-30; Sep. 2005.

Khedr et al.; Therapeutic effect of repetitive transcranial magnetic stimulation on motor function in Parkinson's disease patients; Eur J Neurol; 10(5):567-72; Sep. 2003.

Kleinjung et al.; Transcranial magnetic stimulation: a new diagnostic and therapeutic tool for tinnitus patients; Int Tinnitus J.; 14(2):112-8; Jul./Dec. 2008.

Lang et al.; Bidirectional Modulation of Primary Visual Cortex Excitability: A Combined tDCS and rTMS Study; Investigative Ophthalmology and Visual Science; 48(12): 5782-5787; Dec. 2007.

Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56 (9): 634-639; Nov. 1, 2004.

Mansur et al.; A sham stimulation-controlled trial of rTMS of the unaffected hemisphere in stroke patients; Neurology; 64(10):1802-4; May 24, 2005.

Nitsche et al.; Excitability changes induced in the human motor cortex by weak transcranial direct current stimulation; Journal of Physiology; 527(3):633-639; Sep. 15, 2000.

O'Reardon et al.; Efficacy and safety of transcranial magnetic stimulation in the acute treatment of major depression: a' multisite randomized controlled trial; Biol Psychiatry; 62(11):1208-16; Dec. 1, 2007.

Ragert et al.; Improvement of spatial tactile acuity by transcranial direct current stimulation; Clin. Neurophysiol.; 119(4):805-11; Apr. 2008 (author manuscript).

Roizenblatt et al.; Site-specific Effects of Transcranial Direct Current Stimulation on Sleep and Pain in Fibromyalgia: A Randomized, Sham-controlled study; Pain Practice; 7(4): 297-306; Dec. 7, 2007.

Sparing et al.; Enhancing language performance with non-invasive brain stimulation R A transcranial direct current stimulation study in healthy humans; Neuropsychologia; 46(1): 261-268; Jan. 15, 2008.

Theodore et al.; Transcranial magnetic stimulation for the treatment of seizures: a controlled study; Neurology; 59(4):560-2; Aug. 27, 2002.

Zanette et al.; The effect of repetitive transcranial magnetic stimulation on motor performance, fatigue and quality of life in amyotrophic lateral sclerosis; J Neurol Sci.; 270(1-2):18-22; Jul. 15, 2008.

Bodo et al.; The role of multidrug transporters in drug availability, metabolism and toxicity; Toxicol Lett; pp. 140-141; Review; pp. 133-43; Apr. 11, 2003.

Wasan et al.; Lipid transfer protein I facilitated transfer of cyclosporine from low- to high-density lipoproteins is only partially dependent on its cholesteryl ester transfer activity; J Pharmacol Exp Ther; 284(2); pp. 599-605; Feb. 1998.

Schneider et al.; U.S. Appl. No. 13/808,806 entitled "Transcranial magnetic stimulation for altering susceptibility of tissue to pharmaceuticals and radiation," filed Apr. 23, 2013.

Blount et al.; The Influence of Thyroid and Thiouracil on Mice Exposed to Roentgen Radiation; Science; 109(2822); pp. 83-84; Jan. 28, 1949.

Buxton; Pharmacokinetics and Phamacodynamics; Goodman & Gilman's The Pharmacological Basis of Therapeutics (11th Ed.); McGraw-Hill , © 2006; pp. 1-23; pub. date Oct. 28, 2005.

George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.

Kimeldorf et al.; The effect of exercise upon the lethality of roentgen rays for rats; Science; 112(2902); pp. 175-176; Aug. 1950.

Lemaire et al.; Influence of blood components on the tissue uptake indices of cyclosporin in rats; J Pharmacol Exp Ther; 244(2); pp. 740-743; Feb. 1988.

Rubin et al.; Radiosensitivity and radioresistance of tumors; Clinical Radiation Pathology; WB Saunders; Ch. 24, pp. 894-933; Jun. 1968.

Rubin et al.; The Modification of Radiation Response; Clinical Radiation Pathology; WB Saunders; Ch. 26, pp. 973-1008; Jun. 1968.

Smith et al.; Effect of thyroid hormone on radiation lethality; Am J Physiol; 165(3); pp. 639-50; Jun. 1951.

Speer et al.; Opposite effects of high and low frequency rTMS on regional brain activity in depressed patients; Biol Psychiatry; 48(12); pp. 1133-1141; Dec. 15, 2000.

Ueno; Individual differences in radio sensitivity of mice correlated with their metabolic rate; Acta Radiol Ther Phys Biol; 10(4); pp. 427-432; Aug. 1971.

Agnew et al.; Considerations for safety in the use of extracranial stimulation for motor evoked potentials; Neurosurgery; vol. 20; pp. 143-147; Jan. 1987.

Avery et al.; A Controlled Study of Repetitive Transcranial Magnetic Stimulation in Medication-Resistant Major Depression; Biological Psychiatry; vol. 59; pp. 187-194; Jul. 2005.

Barker et al.; Non invasive magnetic stimulation of the human motor cortex; Lancet; vol. 1; pp. 1106-1110; May 1985.

Barker, A. T.; An introduction to the basic principles of magnetic nerve stimulation; Journal of Clinical Neurophysiology; vol. 8; No. 1; pp. 26-37; Jan. 1991.

Basser et al.; Stimulation of myelinated nerve axon by electromagnetic induction; Medical & Biological Engineering and Computing.; vol. 29; pp. 261-268; May 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; (Month Unavailable) 2002.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; Jun. 2003.

(56) References Cited

OTHER PUBLICATIONS

Davey et al.; Prediction of magnetically induced electric fields in biologic tissue; IEEE Transactions on Biomedical Engineering; vol. 38; pp. 418-422; May 1991.
Davey et al.; Suppressing the surface field during transcranial magnetic stimulation; IEEE Transactions on Biomedical Engineering; vol. 53; No. 2; Feb. 2006; pp. 190-194.
DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.
Epstein et al.; Magnetic coil suppression of visual perception at an extracalcarine site; J. Clin. Neurophysiól; vol. 13; No. 3; pp. 247-252; May 1996.
George, Mark S.; Stimulating the brain; Scientific American; Sep. 2002; pp. 67-73.
Han et al.; Multichannel magnetic stimulation system design considering mutual couplings among the stimulation coils; IEEE Trans. on Biomedical Engineering; vol. 51; No. 5; pp. 812-817; May 2004.
Hayward et al.; The role of the anterior cingulate cortex in the counting stroop task; Exp Brain Res; vol. 154(3); pp. 355-358; Feb. 2004.
Hemond et al.; Transcranial magnetic stimulation in neurology: What we have learned from randomized controlled studies; Neuromodulation: Technology at the Neural Interface; vol. 10; No. 4; pp. 333-344; 2007.
Hovey, C. et al.; The new guide to magnetic stimulation; The Magstim Company Ltd.; Carmarthenshire, United Kingdom; Oct. 2003; 42 pages.
Hsu et al., Analysis of Efficiency of Magnetic Stimulation; IEEE Transactions on Biomedical Engineering; vol. 50. No. 11; Sep. 2003; pp. 1276-1285.
Huang et al.; Theta Burst Stimulation of the Human Motor Cortex; Neuron; vol. 45; pp. 201-206; Jan. 2005.
Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.
Kamitani et al.; A model of magnetic stimulation of neocortical neurons; Neurocomputing; vol. 38; No. 40; Jun. 2001; pp. 697-703.
Kandel et al.; Chapter 12: Synaptic Integration; Principles of Neural Science; Editors: Kandel, Schwartz and Jessell; 4th Edition, McGraw-Hill; pp. 208-227; Jan. 5, 2000.
Lang et al.; How does transcranial DC stimulation of the primary motor cortex alter regional neuronal activity in the human brain?; Eur. J. Neurosci.; vol. 22; No. 2; pp. 495-504; Jul. 2005.
Lefaucheur, Jean-Pascal; Use of repetitive transcranial magnetic stimulation in pain relief; Expert Rev Neurother; vol. 8, No. 5: pp. 799-808; May 2008.
Lefaucheur et al.; Pain relief induced by repetitive transcranial magnetic stimulation of precentral cortex; Neuroreport; vol. 12, issue 13: pp. 2963-2965; Sep. 17, 2001.
Lefaucheur et al.; Somatotopic organization of the analgesic effects of motor cortex rTMS in neuropathic pain; Neurology; vol. 67, No. 11: pp. 1998-2004; Dec. 12, 2006.
Levkovitz et al.; A randomized controlled feasibility and safety study of deep transcranial magnetic stimulation; Clin. Neurophysiol.; vol. 118(12); pp. 2730-2744; Dec. 2007.
Lin et al.; Magnetic coil design considerations for functional magnetic stimulation; IEEE Trans. on Biomedical Eng.; vol. 47; No. 5; pp. 600-610; May 2000.
Magstim Website: http://www.magstim.com/magneticstimulators/magstimacc/12494.html (printed Mar. 23, 2010).
Martin et al.; Transcranial magnetic stimulation for treating depression; Cochrane Review; (Month Unavailable) 2002 (In (eds.): The Cochrane Library. Oxford: Update Software: The Cochrane Library. Oxford: Update Software.).
Mayberg et al.; Deep brain stimulation for treatment-resistant depression; Neuron; vol. 45; pp. 651-660; Mar. 2005.
Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.
Nadeem et al.; Computation of electric and magnetic stimulation in human head using the 3-D impedance method; IEEE Trans on Biomedical Eng; vol. 50; No. 7; pp. 900-907; Jul. 2003.
Ohnishi et al.; rCBF changes elicited by rTMS over DLPFC in humans; Suppl Clin Neurophysiol.; vol. 57: pp. 715-720; (Month Unavailable) 2004.
Paton et al.; Vascular-brain signaling in hypertension: role of angiotensin II and nitric oxide; Curr. Hypertens Rep; vol. 9; No. 3; pp. 242-247; Jun. 2007.
Rossini et al.; Transcranial magnetic stimulation: Diagnostic, therapeutic, and research potential; Neurology; vol. 68, No. 7: pp. 484-488; Feb. 13, 2007.
Roth et al.; A coil design for transcranial magnetic stimulation of adeep brain regions; J. Clin. Neurophysiology; vol. 19; No. 4; Aug. 2002; pp. 361-370.
Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.
Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.
Ruohonen et al.; (Chapter 2); Magnetic stimulation in clinical neurophysiology; Second Ed.; Ed. Elsevier Inc.; pp. 17-30; (Month Unavailable) 2005.
Ruohonen et al.; Focusing and targeting of magnetic brain stimulation using multiple coils; Medical & Biological Engineering and Computing; vol. 35; pp. 297-301; May 1998.
Sackheim, H. A.; Commentary: Magnetic stimulation therapy and ECT; Convulsive Therapy; vol. 10; No. 4; Dec. 1994; pp. 255-285.
Sekino et al.; Comparison of current distributions in electroconvulsive therapy and transcranial magnetic stimulation; J. of Applied Physics; vol. 91; No. 10; pp. 8730-8732; May 15, 2002.
Speer et al.; Opposite effects of high and low frequency rTMS on regional brain activity in depressed patients; Biol. Psychiatry; vol. 48; No. 12; pp. 1133-1141; Dec. 15, 2000.
Takano et al.; Short-term modulation of regional excitability and blood flow in human motor cortex following rapid-rate transcranial magnetic stimulation; Neuroimage; vol. 23; No. 3; pp. 849-859; Nov. 2004.
Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.
Ueno et al.; Localized stimulation of neural tissues in the brain by means of a paired configuration of time-varying magnetic fields; J. Appl. Phys.; vol. 64; No. 10; pp. 5862-5864; Nov. 15, 1988.
Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.
Wagner et al.; Three-dimensional head model simulation of transcranial magnetic stimulation; IEEE Trans. on Biomedical Engineering; vol. 51; No. 9; pp. 1586-1598; Sep. 2004.
Wagner et al.; Transcranial direct current stimulation: A computer-based human model study; NeuroImage; vol. 35; issue 3; Apr. 15, 2007; pp. 1113-1124.
Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.
Wasserman et al.; Therapeutic application of repetitive magnetic stimulation: a review; Clinical Neurophysiology; vol. 112; pp. 1367-1377; Apr. 2001.
Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; Jan. 1998.

(56) References Cited

OTHER PUBLICATIONS

Xiao et al.; Magnetic Nanocomposite Paste: An Ideal High- µ, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.

Yu et al.; Pathogenesis of normal-appearing white matter damage in neuromyelitis optica: diffusion-tensor MR imaging; Radiology; vol. 246, No. 1: pp. 222-228; Jan. 2008.

Mishelevich et al.; U.S. Appl. No. 12/680,912 "Transcranial magnetic stimulation with protection of magnet-adjacent structures," filed Mar. 31, 2010.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Mishelevich et al.; U.S. Appl. No. 12/990,235 entitled "Transcranial magnetic stimulation by enhanced magnetic field perturbations," filed Oct. 29, 2010.

Schneider, M. Bret .; U.S. Appl. No. 13/169,967 entitled "Enhanced Spatial Summation for Deep-Brain Transcranial Magnetic Stimulation," filed Jun. 27, 2011.

Sadler, John W.; U.S. Appl. No. 13/512,496 entitled "Power Management in Transcranial Magnetic Stimulators," filed May 29, 2012.

Schneider et al.; U.S. Appl. No. 13/877,428 entitled "Transverse transcranial magnetic stimulation coil placement for improved analgesia," filed Jun. 27, 2013.

Schneider et al.; U.S. Appl. No. 13/888,263 entitled "Transverse transcranial magnetic stimulation for improved analgesia," filed May 6, 2013.

* cited by examiner

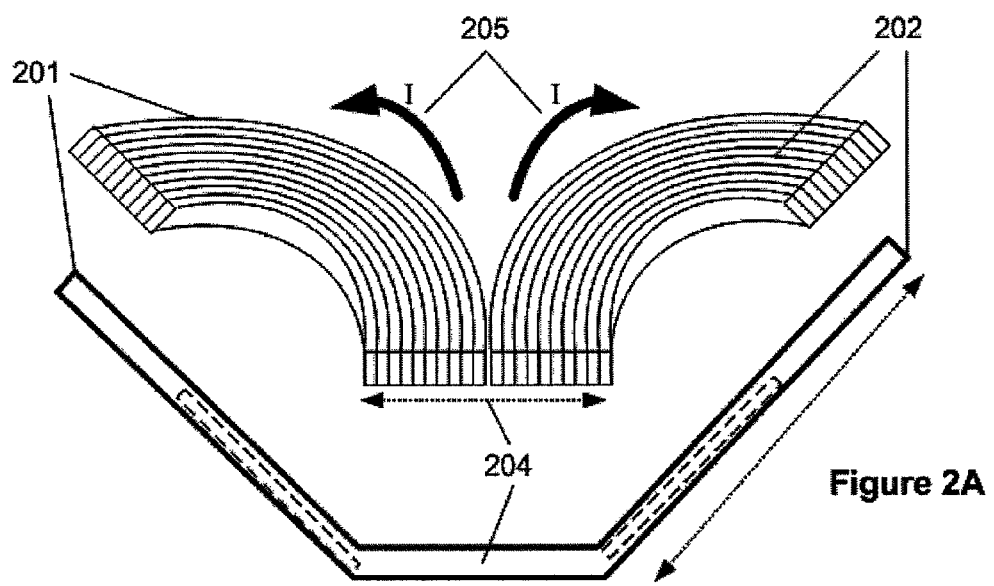
Figure 2A
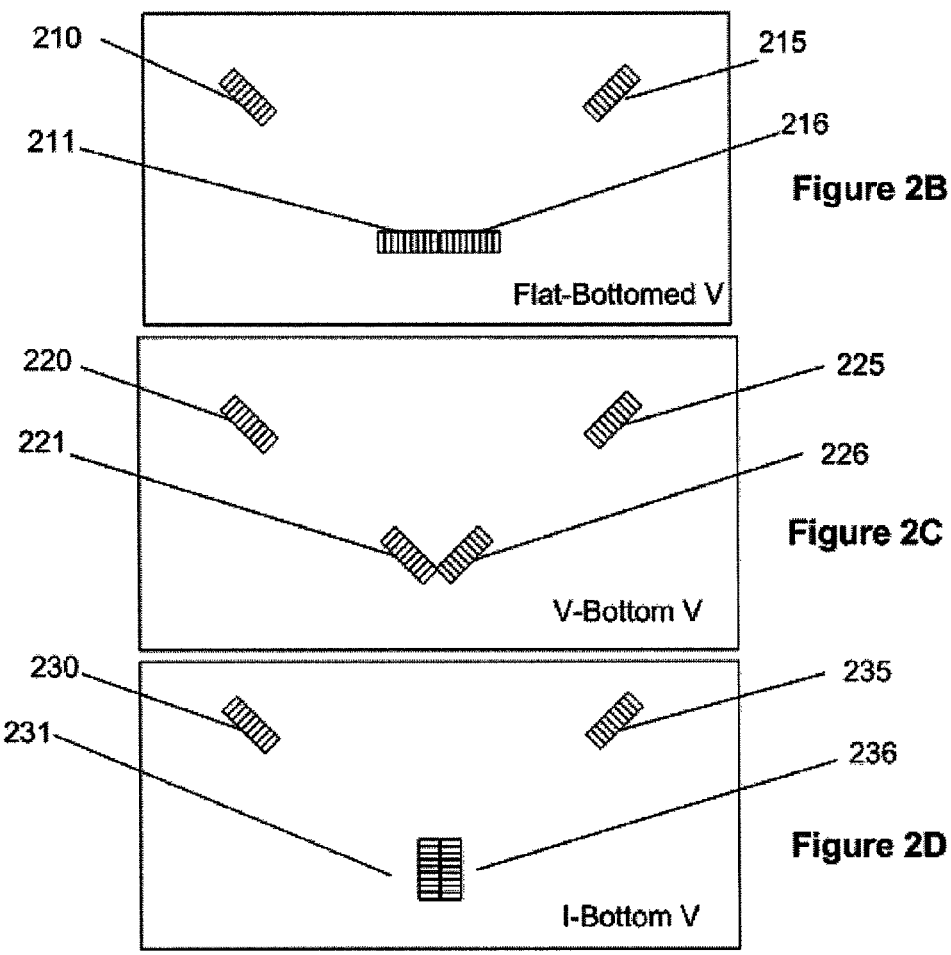
Figure 2B
Flat-Bottomed V
Figure 2C
V-Bottom V
Figure 2D
I-Bottom V

SHAPED COILS FOR TRANSCRANIAL MAGNETIC STIMULATION

CROSS REFERENCE TO RELATED APPLICATIONS

This application claims priority to U.S. Provisional patent application Ser. No. 61/143,103, titled "SHAPED COILS FOR TRANSCRANIAL MAGNETIC STIMULATION", filed on Jan. 7, 2009.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and methods described herein relate generally to the focusing of magnetic fields generated by electromagnets used for Transcranial Magnetic Stimulation (TMS). In particular, shaped coil pairs that are advantageous for TMS are described.

BACKGROUND OF THE INVENTION

A typical Transcranial Magnetic Stimulation (TMS) electromagnet includes a pair of coils that are joined to form a flat figure-8 shaped electromagnet. Such figure-eight double coil magnets are well known, for instance the 70 mm double-coil configuration from Magstim (e.g., Model 9925, Magstim Ltd., Wales, UK). The electromagnets can be powered by commercially available power sources such as the "Magstim Rapid[2]" (Magstim Ltd., Wales, UK) that provides electrical currents for pulsed magnetic fields. The magnetic field projected from standard figure-8 shaped double coil electromagnets is not optimal for deep brain stimulation, however. In particular, the depth and shape of the emitted field is limited.

For conventional circular and double circular coils, the Biot-Savart law dictates that magnetic field strength declines as a function of distance from face of a coil. This makes focal stimulation of the brain challenging to achieve at the cortical surface (beneath scalp, skull and meninges), and even more difficult beneath the cortical surface.

Alternative configurations for TMS electromagnets have been proposed, including those described in Zangen et al. (U.S. Patent applications publication Nos. 2006/0287566 and 2004/0078056). Alternative designs have likewise been proposed in Levkovitz Y, Roth Y, Harel EV, Braw Y, Sheer A, Zangen A, "A randomized controlled feasibility and safety study of deep transcranial magnetic stimulation." Clin. Neurophysiol. 118(12):2730-44 (December 2007).

However, the proposed designs described above each have substantial disadvantages, particularly with regard to the specificity and control of the magnetic field generated, as well as the ease with which these magnets may be fabricated and characterized. Described herein are TMS electromagnets configured to address many of the problems described above. In particular, the inventors have found that, unexpectedly, TMS electromagnets formed from coils that are not linear, but are instead curved or bent to form a "V", "U" or "Y" may result in magnetic field intensities that are well suited for deep-brain TMS.

The coils described herein for TMS may therefore be designed to accommodate a difficult balance between focality, and power level delivered to a target. This balance has been particularly difficult to achieve with known TMS electromagnets, yet is of great importance when the target is below the cortical surface of the brain.

Examples of systems, devices and methods that may benefit from the TMS coils described herein may be found, for example, in any of the following applications: Patent Application No. PCT/US2008/071663, (titled "DEVICE AND METHOD FOR TREATING HYPERTENSION VIA NON-INVASIVE NEUROMODULATION") filed Jul. 30, 2008; Patent Application No. PCT/US2008/072930, (titled "GANTRY AND SWITCHES FOR POSITION-BASED TRIGGERING OF TMS PULSES IN MOVING COILS") filed Aug. 12, 2008; Patent Application No. PCT/US2008/073751, (titled "FIRING PATTERNS FOR DEEP BRAIN TRANSCRANIAL MAGNETIC STIMULATION"), filed Aug. 20, 2008; Patent Application No. PCT/US2008/075575 (titled "FOCUSING MAGNETIC FIELDS WITH ATTRACTOR MAGNETS AND CONCENTRATOR DEVICES"), filed Sep. 8, 2008; Patent Application No. PCT/US2008/075583 (titled "PITCH, ROLL, AND YAW MOTIONS FOR ELECTROMAGNET ARRAYS"), filed Sep. 8, 2008; Patent Application No. PCT/US2008/075706 (titled "FOCUSED MAGNETIC FIELDS"), filed Sep. 9, 2008; Patent Application No. PCT/US2008/075824 (titled "AUTOMATED MOVEMENT OF ELECTROMAGNETS TRACKING ECCENTRICITY OF THE HEAD"), filed Sep. 10, 2008; Patent Application No. PCT/US2008/077851 (titled "SYSTEMS AND METHODS FOR COOLING ELECTROMAGNETS FOR TRANSCRANIAL MAGNETIC STIMULATION"), filed Sep. 26, 2008; Patent Application No. PCT/US2008/079378 (titled "DISPLAY OF MODELED MAGNETIC FIELDS"), filed Oct. 9, 2008; Patent Application No. PCT/US2008/081048 (titled "INTRA-SESSION CONTROL OF TRANSCRANIAL MAGNETIC STIMULATION"), filed Oct. 24, 2008; Patent Application No. PCT/US2008/081307 (titled "TRANSCRANIAL MAGNETIC STIMULATION WITH PROTECTION OF MAGNET-ADJACENT STRUCTURES"), filed Oct. 27, 2008; U.S. patent application Ser. No. 12/324,227 (titled "TRANSCRANIAL MAGNETIC STIMULATION OF DEEP BRAIN TARGETS"), filed Nov. 26, 2008; U.S. patent application Ser. No. 12/185,544 (titled "MONOPHASIC MULTI-COIL ARRAYS FOR TRANCRANIAL MAGNETIC STIMULATION"), filed Aug. 4, 2008; and Patent Application No. PCT/US2008/072154 (titled "MONOPHASIC MULTI-COIL ARRAYS FOR TRANSCRANIAL MAGNETIC STIMULATION"), filed Aug. 4, 2008.

SUMMARY OF THE INVENTION

The present invention provides an improved design for magnetic brain stimulation coils. This coil design (generally referred to as a "V-shaped coil" may yield a substantially improved penetration to depth. In particular the "I-bottomed V-shaped coils" (also referred to as the Y-shaped coils) are of particular interest, and have been found to have unexpectedly superior magnetic field profiles for use in TMS.

For example, described herein are Y-shaped Transcranial Magnetic Stimulation (TMS) electromagnets configured to emit a focused magnetic field. These TMS electromagnets may include: a first bent magnetic coil loop comprising a plurality of windings and a second bent magnetic coil loop comprising a plurality of windings; wherein the first magnetic coil loop comprises a first inner coil region and the second magnetic coil loop comprises a second inner coil region, and wherein the first and second inner coil regions are arranged to form a vertex configured so that the plurality of windings within the first inner coil region for a column this is adjacent and parallel to the plurality of windings within the second inner coil that are arranged in a column; and wherein the first magnetic coil loop comprises a first outer coil region and the second magnetic coil loop comprises a second outer coil region, and the angle between the first outer coil region and the second outer coil region is between about 30 degrees and about 120 degrees.

The first outer coil region may be located opposite the first inner coil region on the first magnetic coil loop and wherein the second outer coil region is opposite the second inner coil region on the second magnetic coil loop.

In some variations, the first bent magnetic coil loop comprises greater than 5 windings. In some variations, the angle between the first outer coil region and the second outer coil region is approximately 60 degrees.

The TMS electromagnet may also include a structural support matrix surrounding the first and second bent magnetic coil loops.

The first and second bent magnetic coil loops may be electrically connected so that the current flows from the first coil loop into the second coil loop. Further, the vertex is configured so that current will flow in the same direction in the first and second inner coil regions of the vertex.

The first and second bent magnetic coil loops may be arranged symmetrically about the vertex. The first and second bent magnetic coil loops may have approximately the same shape and size, or they may be different sizes.

Also described herein are shaped coil Transcranial Magnetic Stimulation (TMS) electromagnet comprising: a first bent magnetic coil loop comprising a column formed of a plurality of conductive windings; a second bent magnetic coil loop comprising a column formed of a plurality of conducive windings; and a vertex region connecting the first and second bent magnetic coil loops; wherein the vertex region is formed by aligning the columns of conductive windings within the first bent magnetic coil loop in parallel with the column of conductive windings within the second bent magnetic coil loop; wherein the angle between a first outer coil region of the first magnetic coil loop and a second outer coil region of the second magnetic coil loop is less than 120 degrees.

The vertex region may comprise an interleaved vertex, as described in greater detail below, or the vertex region may comprise an I-bottomed vertex (the I-bottomed vertex may be considered a sub-set of the interleaved vertex).

The first outer coil region may be the region of the coil(s) opposite the vertex region on the first magnetic coil loop and wherein the second outer coil region is opposite the vertex region on the second magnetic coil loop.

The first magnetic coil loop may comprise greater than 5 windings.

In some variations the angle between a first outer coil region of the first magnetic coil loop and a second outer coil region of the second magnetic coil loop is approximately 60 degrees.

As mentioned, the shaped TMS electromagnet my further comprising a structural support matrix surrounding the first and second magnetic coil loops.

The first and second bent magnetic coil loops may be electrically connected so that the current flows from the first bent magnetic coil loop into the second bent magnetic coil loop. Further, the vertex may be configured so that current will flow in the same direction in the portion of the windings forming the first and second bent magnetic coil loops that are part of the vertex.

Also described herein are shaped coil Transcranial Magnetic Stimulation (TMS) electromagnets comprising: a first bent magnetic coil loop comprising a plurality of conductive windings; a second bent magnetic coil loop comprising a plurality of conducive windings; and a generally V-shaped bottom vertex region between the first and second bent magnetic coil loops; wherein the angle between an outer coil region of the first bent magnetic coil loop and the outer coil region of the second bent magnetic coil loop is between about 55 and about 65 degrees; and wherein the V-shaped bottom vertex region is formed by arranging immediately adjacent portions of the each coil at an angle of between about 70 and about 110 degrees relative to each other.

Also described herein are shaped Transcranial Magnetic Stimulation (TMS) electromagnet comprising: a first bent magnetic coil loop formed of a column comprising a plurality of windings; a second bent magnetic coil loop formed of a column comprising a plurality of windings; a flat-bottomed vertex region between the first and second bent magnetic coil loops; wherein the angle between an outer coil region of the first bent magnetic coil loop and the outer coil region of the second bent magnetic coil loop is between about 55 and about 65 degrees; and wherein the flat-bottom vertex region is formed by arranging an inner coil region of the first bent magnetic coil loop immediately adjacent to an inner coil region of the second bent magnetic coil loop so that the column of windings forming the first and second inner coil regions are at an angle of approximately 180 degrees with respect to each other.

BRIEF DESCRIPTION OF THE DRAWINGS

FIG. 2A shows a partial cross-section through a TMS electromagnet having a pair of coils oriented in a "U" configuration, also referred to as a "flat-bottomed V-shaped coil pair".

FIG. 2B is a cross-section through a flat-bottomed V-shaped coil pair (or "U"-shaped coil pair).

FIG. 2C is a cross-section through a V-shaped coil pair.

FIG. 2D is a cross-section through an I-bottomed V-shaped coil pair (or "Y"-shaped coil pair).

DETAILED DESCRIPTION

Figure 1:
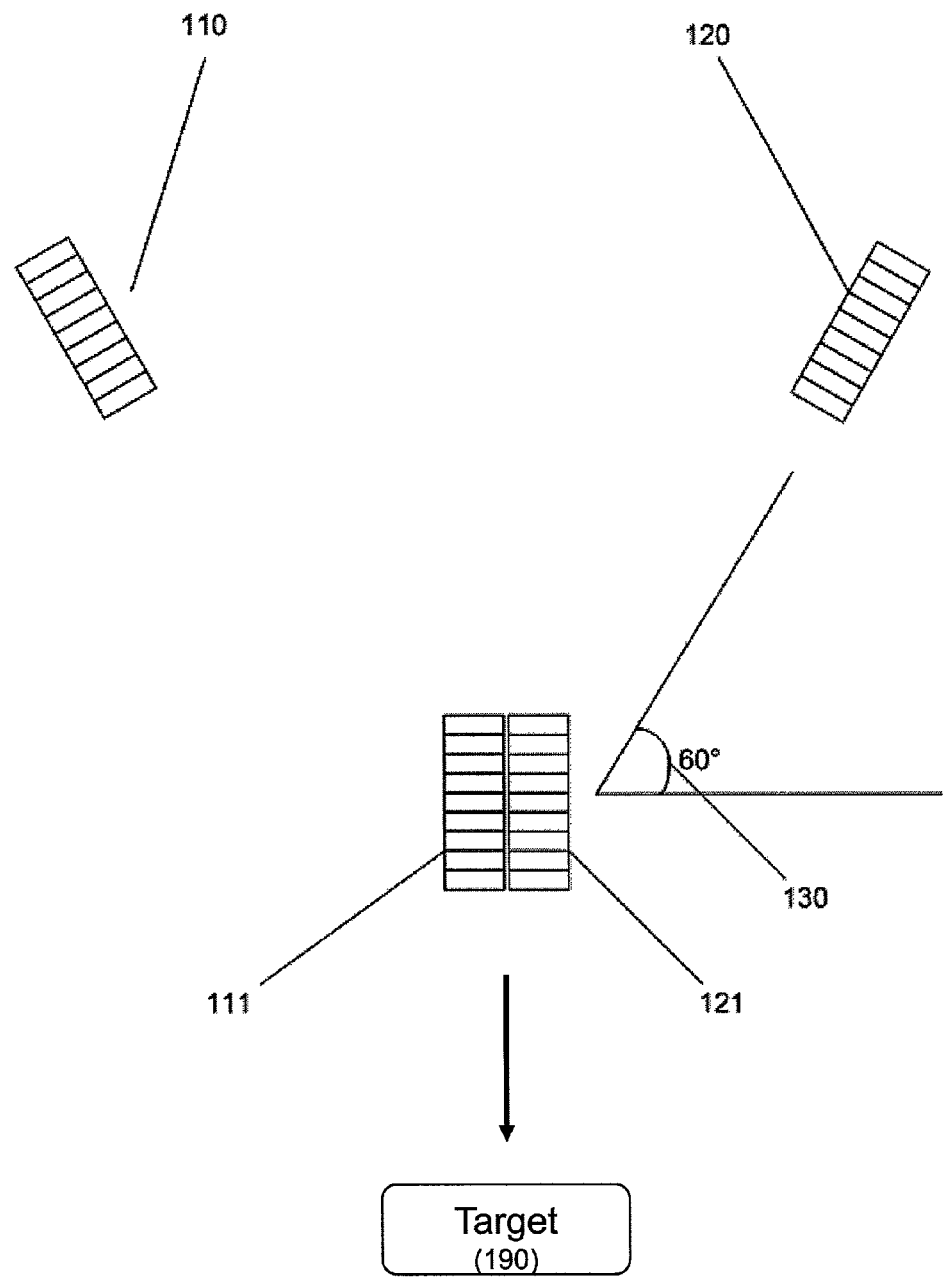
FIG. 1 shows a cross-section though a TMS electromagnet having a pair of coils oriented in a "Y" configuration, also referred to as an "I-bottomed V-shaped coil pair".

In general, the TMS magnets described herein may be referred to as shaped-coil TMS magnets. A shaped-coil TMS magnet typically includes a pair of coils (each having multiple windings) that have a non-flat shape and are connected to each other at a vertex region or point. A shaped coil may have a bent or curved ring shape. The shaped coils described herein may also be referred to as "V-shaped" coils.

Prior art TMS magnets having a two coils were typically "flat," forming a "figure-8" shape. The shaped-coil TMS magnets described herein generally have two coils that are at an angle with each other that is less than 180 degrees (an angle of 180 degrees corresponds to the standard "figure-8" shaped coils), and an angle with respect to a horizontal plane that is greater than zero (e.g., a standard "figure-8" shaped coil has an angle of 0 degrees with respect to the horizontal). The vertex region, which may also be referred to as the 'bottom' of the shaped coil pairs, may be flat (e.g., the coils are connected end-to-end with a local angle relative to each other of 180°), parallel (e.g., the coils are connected so that the stack of windings for each coil are parallel with the stack of windings of the other coil), V-shaped (e.g., the stack of windings for each coil are angled with respect to each other), or intermingled/interleaved (e.g., the windings of each coil overlap with each other). From the vertex region, both coils typically extend outwards, subtending an angle that is less than 180 degrees. The "angle" of the TMS electromagnet may refer to the angle by which the coils are bent from the horizontal, starting from the standard figure-8 coil configuration. As illustrated below, the angle of the TMS electromagnet may be varied, but in some variations the minimum angle between the outermost portions of the rings is approximately 60 degrees.

The two coils are typically in electrical continuity, so that the windings of one coil are continuous with the windings of the other coil. Coils are typically wound in opposite directions, thus current will flow in opposite directions in each coil. The current though each coil at the vertex region flows in the same direction. The windings of the two coils are connected through a crossover region, where the windings forming one coil become continuous with the windings forming the other coil. The crossover region may occur at the vertex area (e.g., where the adjacent coils meet), or may be anywhere else between the coils. The crossover region may go from the central turn of one coil to the central turn of the other coil.

A coil may be formed of any number of windings. For example, the coil may be between 8 and 12 windings, between 9 and 11 windings, between 9 and 10 windings, etc. In some variations the coils are formed from copper flat wire, e.g., 0.984 inch by 0.240 inch wire), though any appropriate conductor may be used. As mentioned above, the coils forming a TMS electromagnet are typically wound in opposite directions.

As mentioned, the coil typically forms a ring or loop of many adjacent windings. The stack of windings may form a rectangle when viewed as a cross-section through the loop. Thus, a cross-section through a coil may include two side surfaces (which may be the long edges) formed by the edges of all of the windings in the stack, separated by an outer surface and an inner surface (formed by the outer winding and inner winding, respectively). The side surfaces of the coil are typically curved, forming the bent ring shape of each coil.

In many of the examples described herein the pair of coils forming the shape-coil TMS magnets are symmetric with respect to each other. Thus, they are typically the same size (including number of windings) and shape. However, in some variations the shapes of the two coils may be different. For example, in some variations the two shaped coils forming the TMS magnet may be of different sizes. In one variation, one shaped coil has more windings than the other shaped coil. In some variations one coil has a different shape than the other coil. For example, in some variations one coil has a different curvature of bending than the other coil.

In some variations the coils are generally circular rings formed by the windings of the conductor. The coil does not necessary have to be circular, but could be oval polygonal, or the like.

FIG. 1 is a cross-section though one variation of a shaped coil having an I-bottom configuration. In this variation, the vertex (the connection between the two coils) is formed so that the stacks of windings of each of the two coils are arranged parallel to each other. Thus, the cross-section appears to roughly form the endpoints of a "Y" shape, with the bottom portion of the "Y" being the parallel and adjacent windings of the coils at the vertex (the inner coil region). In FIG. 1, the cross-section through the first outer coil region 110 is part of the same shaped coil (subcoil A) as the cross-section through the first inner coil region 111, and the cross-section through the second outer coil region 120 is part of the same shaped coil (subcoil B) as the cross section through the second inner coil region 121. The cross-section of the two inner coil regions 111, 121 are parallel. The maximum angle of this variation of shaped coil TMS electromagnet is illustrated 130 as the angle between the upper margin of subcoil B and the normal (flat) plane. In this embodiment, this angle is 60 degrees. The maximum angle between the bent wings of the coils is also 60 degrees. The angle at the outermost edges of the coil from the vertex where the coils meet may be referred to as the angle of the shaped coil TMS electrode. In FIG. 1, this angle is 60°, both relative to the two coils (the "wings" of the coils) and relative to a plane that is perpendicular to the axis of symmetry though the vertex. The angle of the shaped coil TMS electromagnet in some variations may be any value between 15 and 75 degrees relative to the perpendicular plane (angle 130 in FIG. 1). Equivalently, the angle between the outermost coil regions of the shaped coils may be between about 150° and 30°.

The inventors have found that the field emitted by the shaped coil TMS electromagnet shown in FIG. 1 is generally directed downward, towards the target 190, as indicated in FIG. 1. This field is shaped so that is more focused compared to a comparable "flat" (i.e., figure-8) TMS coil.

FIG. 2A shows another variation of a V-shaped TMS electromagnet. In FIG. 2A, the shaped coil TMS electromagnet has a flat bottom, and may be referred to as a flat bottomed TMS electromagnet (or "flat bottomed V-shaped TMS electromagnet"). In this variation, the first (or "A") subcoil 201 is adjacent to the second (or "B") subcoil 202 so that the vertex between the two is a flat region having a zone of mutual induction 204 where subcoils A and B meet. The direction of electrical current in coils 205 is indicated, illustrating that current flows in opposite directions in the coils (e.g., clockwise/counterclockwise), and is oriented in the same direction at the region where the coils form the vertex 204. In general, the current in the vertex region between the two coils may travel in the same direction, thereby inducing a consistent magnetic field.

In the example shown in FIG. 2A, the angle of the shaped coil TMS electromagnet is approximately 45 degrees relative to the horizontal, as indicated in the cross-sectional schematic shown below the partial sections through the two coils. Thus, the angle between the outer coil regions is approximately 90°. In some variations, the angle between the outer coil regions is less than 90°, for example, between about 45° and about 80° (e.g., between about 55° and about)60°. In some variations the angle is greater than 90° (e.g., between about 100° and 170°, between about 110° and 160°, between about 120° and 150°, etc.).

Figure 2E:
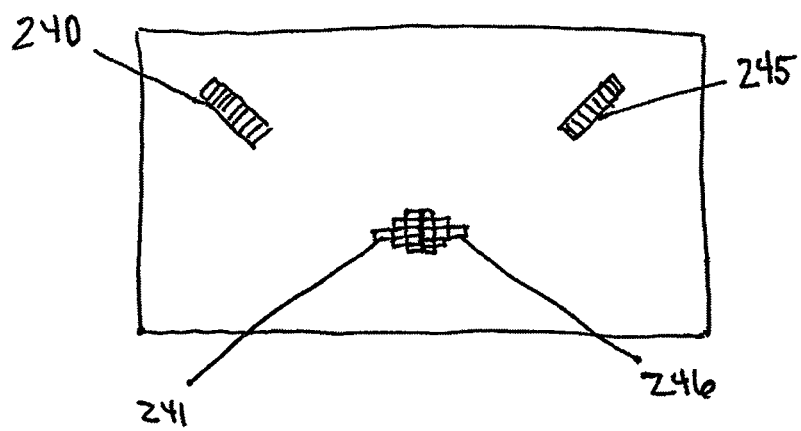
FIG. 2E is a cross-section through another V-shaped coil pair having a central section that is maximized for contact between the central members of the coils.

FIGS. 2B to 2E illustrate various V-shaped TMS electromagnets having different configurations. Each of these exemplary TMS electromagnets has a coil angle of 60 degrees, however the arrangement of the vertex is different. For example, FIG. 2B shows a cross-section though another variation of a flat-bottomed V-shaped TMS electromagnet. The variation may be referred to as a generally "U" shaped profile, because of the substantially flat bottom of the vertex region. The angles between the cross-sections of the outer coil regions 210, 215 of the two subcoils in this example is approximately 60 degrees. The angle between the cross-sections of the inner coil regions 211, 216 is 180° (or 0° relative to the horizontal plane). Thus, the inner coil regions of the two coils are arranged so that they are side-by-side, forming the flat bottom.

FIG. 2C shows a cross-section through the TMS electromagnet in which the outer coil regions 220, 225 of each coil are oriented in the same direction as the cross-section through the inner coil regions 221, 226 for each coil. The two coils have an angle between them of 60 degrees relative both to each other and to the horizontal. Thus, both of the lower regions forming the vertex are angled 60 degrees from the horizontal. This shape may be similar to the other commercially available "butterfly" double coils, although oriented opposite the variation shown here, and may have the same drawbacks inherent in those magnets. In particular, such a butterfly coil does not include a central planar region where the coils meet (the vertex). This may result in a weaker field, since the each subcoil is wound in a single plane, and the two flat plane components are offset by an angle.

FIG. 2D illustrates another variation of an I-bottomed TMS electromagnet. In this variation, the outer coil regions 230, 235 are both angled 60 degrees from the horizontal (and relative to each other), but the cross-section through the inner coil regions at the vertex show that two inner coil regions are parallel (angled 90° with the horizontal and 0° relative to each other).

FIG. 2E shows an example of a shaped coil TMS electromagnet having an interleaved bottom region. In this example, the windings forming the bottom region of the vertex are not stacked in a single column, but are some of them run adjacent to each other for at least part of the region forming the vertex. The outer coil regions of each coil remain wound in a single (stacked) column). Thus the vertex (bottom or base region of the magnet) maximizes the contact between the adjacent windings of each coil while minimizing the distance from the coils to the target. The coil windings at the inner coil region (in the vertex region) for each coil may be arranged to form a flat surface that can abut a similar flat surface on the adjacent coil. In some variations the coil windings between the two regions 241, 246 may overlap with each other. In FIG. 2E, the coil windings of the joined coils 241, 246 forming the vertex are organized so that they have an approximately circular cross-section. The cross-sections 241, 246 of the vertex inner coil regions are shown having nine rectangular windings; as mentioned above, other shapes of winding material (circular cross-sections, etc.), as well as coils having more or fewer windings may be used.

Figure 2F:
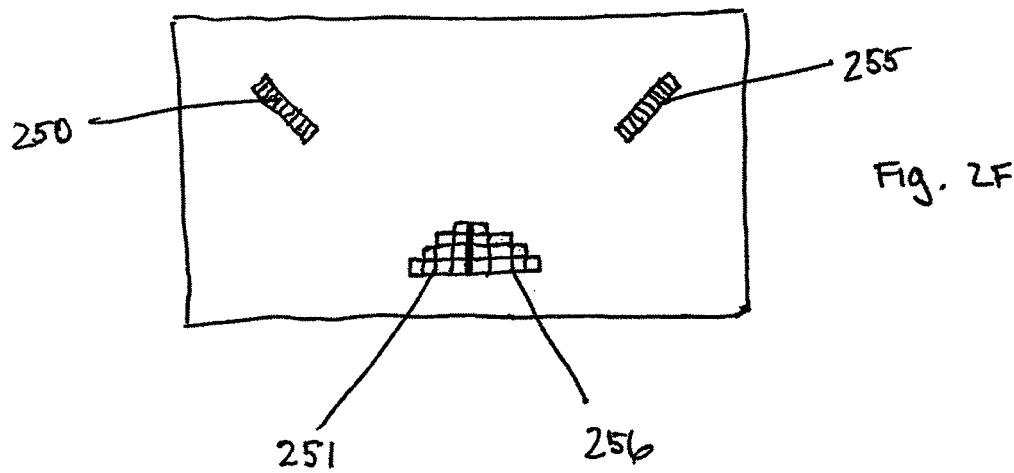
FIG. 2F is a cross-section through another V-shaped coil pair having a central section that is maximized for contact between the central members of the coils.

FIG. 2F shows another variation of a shaped coil TMS electromagnet with an interleaved bottom. These regions are referred to as "interleaved" because the windings forming the vertex region for the coils are not strictly wound in a stacked column, but may overlap or be wound next to each other, as shown. In FIG. 2F, the vertex region of the TMS electromagnet has a triangularly shaped cross-section for the coils. In FIG. 2F the vertex is again formed by maximizing the contact between the adjacent coils while minimizing the distance from the coils to the target. In the variation shown in FIG. 2F, the coil windings have been organized so that they form an approximately triangular cross-section, having a flat surface that faces the target direction. The cross-sections 251, 256 through the inner coil regions are shown with ten rectangular windings, and the outer coil regions 250, 255 are each at a 60 degree angle with the horizontal in this example. Any of the angles described above may be used for the coils. For example, the wings of the TMS electromagnet may be separated by between about 60° and about 150°.

Figure 3A:
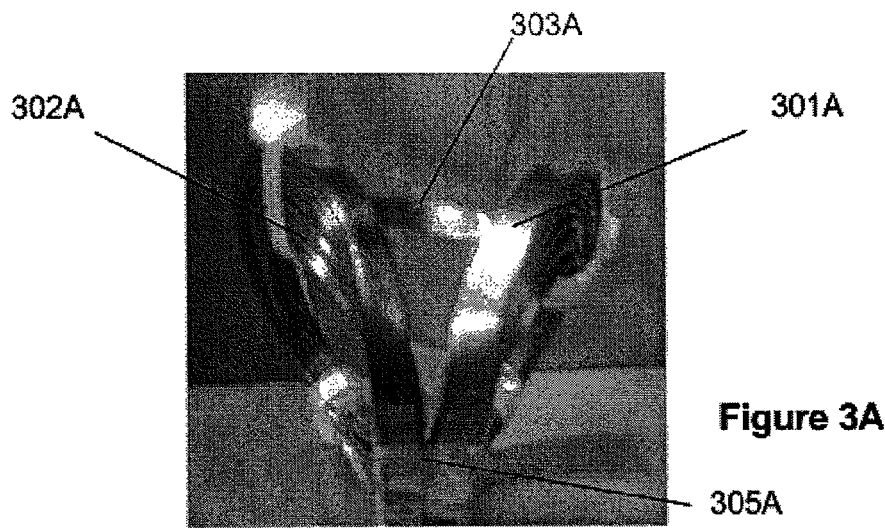
FIG. 3A through 3C show different perspective views of one variation (shown here as a mock-up model) of an I-bottomed V-shaped coil pair.
Figure 3B:
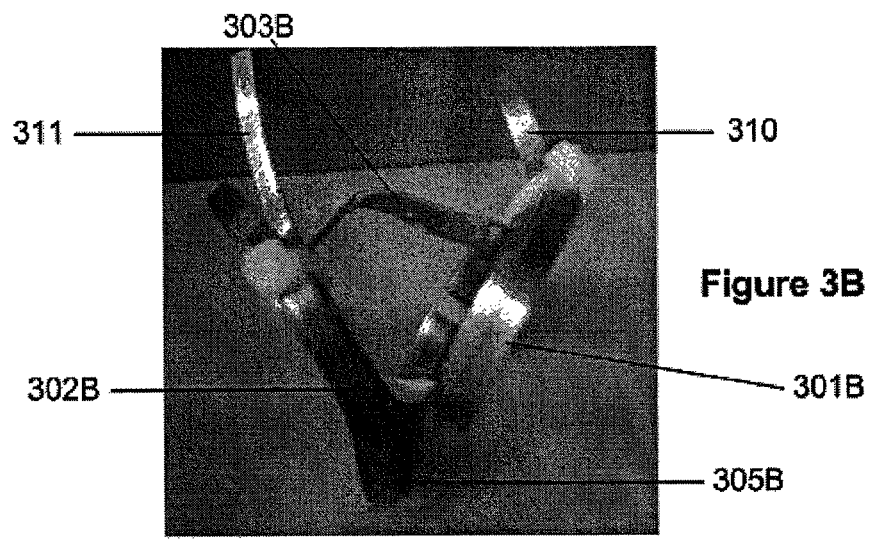
Figure 3C:
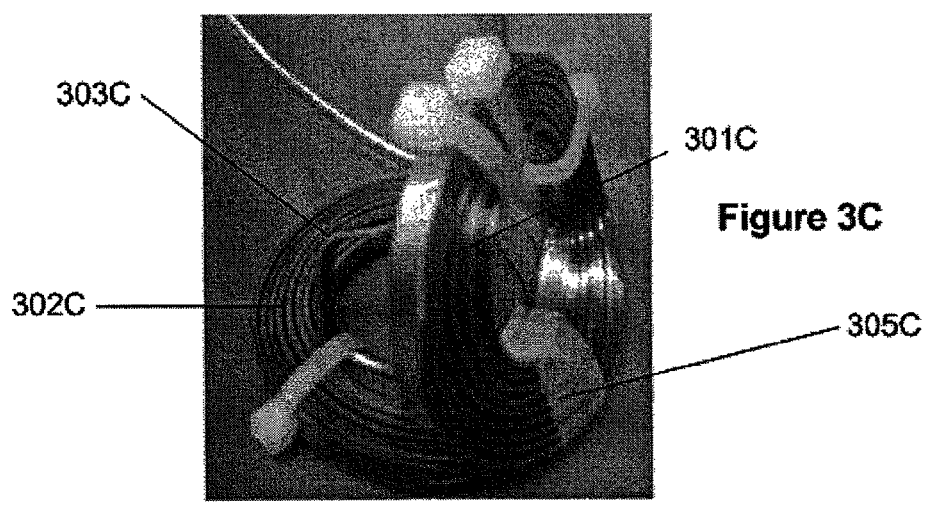

FIGS. 3A to 3C illustrate one variation of an I-bottomed (Y-shaped) TMS electromagnet, similar to the one shown in cross-section in FIG. 1 and FIG. 2D. In FIG. 3A the two coils forming the TMS electromagnet include a first subcoil 302 (subcoil A) and a second subcoil 301 (subcoil B). The two subcoils meet in a vertex region 305. This central section (vertex) is in a substantially perpendicular orientation with respect to the target, as illustrated in FIG. 1 by the arrow. The emitted field will be directed towards the target in this direction. The portions of the subcoils 301, 302 forming the vertex 305 are substantially parallel in the vertex region, as better seen in FIG. 3B.

The crossover region 303 shown in FIG. 3A-3C extends between the central loops of the two coils, and is not located in the vertex region, although it could be. These figures also illustrate the connections to the power source for the coils 310, 311. For example, a TMS electromagnet may be electrically connected to a power source to provide an electrical current that is pulsed with a magnitude of about 5000 A.

Figure 4:
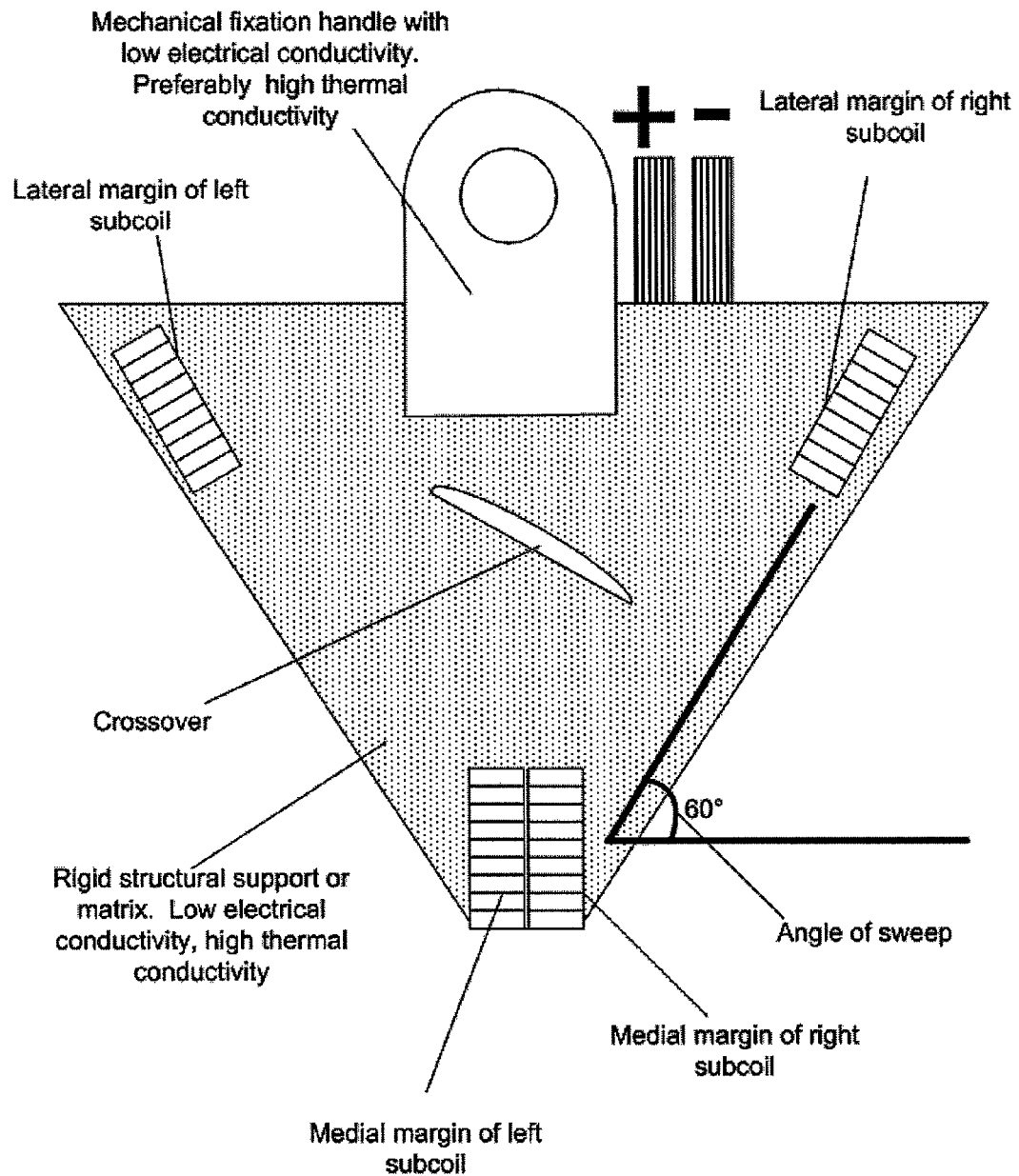
FIG. 4 is one example of a TMS electromagnet as described herein.

Any of the TMS electromagnets described herein may also include a support structure. FIG. 4 shows one variation of a shaped coil TMS electromagnet secured to a support structure. The TMS electromagnet in this example is a Y-shaped shaped coil TMS electromagnet similar to those described above. This example includes two concentric double (sub) coils of approximately the same diameter windings as a standard 70 mm double coil. The inner coil region of each subcoil (of the double coil structure) forming the vertex are placed side-by-side vertically, and the outer coil regions of the loops are swept to 60 degrees from the horizontal plane (with an angle between the outer coil regions of 60°). This variation may be constructed using a single length of flat wire, with no solder at the crossover.

The structural support matrix may completely or partially surround the coils. The structural support matrix may provide support and protect against mechanical shock. Mechanical shock forces may be created in making and/or operation of the TMS electromagnet, particularly in the lateral wings, so a structural support matrix (which may be rigid) may be used. This support structure may be formed of a low electrical conductivity and high thermal conductivity material. In some variations, the support structure may be a hollow strut system that facilitates cooling by air flow/convection, or a solid matrix for heat conduction. The support structure may be filled with a fluid to assist in heat transfer.

In general, the shaped coil TMS electromagnets described herein include two coils that are arranged so that the outer portions of each coil (subcoil) are at an angle with respect to the horizontal, and the vertex of the coils, where they are immediately adjacent to each other, may be arranged at a different angle, or to maximize the contact between the loops of the two coils while also maximizing the portion of the coils nearest the target. For example, in one variation an I-bottomed V-shaped TMS electromagnet is configured so that the outer portions of each coil are at an angle of 60 degrees with respect to the horizontal (also forming an angle of 60 degrees between them), while the vertex region of the TMS electromagnet is formed by placing the coils regions parallel to each other, so that the vertex region of each coil forms an angle of 90 degrees with the horizontal. In all of these cases the "horizontal" direction will correspond to the plane of the target. The horizontal direction is also perpendicular to the axes of symmetry for the coils.

In some variations the TMS electromagnets described herein may be defined by the angles formed by the outer portion of the coils with horizontal and the angles formed by the inner or vertex portions of the coil with the horizontal. The angle formed by the outer portion of the coils may be around about 60 degrees (e.g., between about 50 and about 70 degrees, between about 45 and about 75 degrees, between about 55 and about 65 degrees, etc.) The angle formed by the inner or vertex portion may be any angle between 0 and 90 degrees. In particular, the angle may be 90 degrees. In still other variations, the loops of the coils forming the vertex are arranged to maximize the contact between loops of adjacent coils. For example, the coils may be arranged so that the loops of each coil in the vertex region form a semicircle that combine to form a circle. In one variation, the coils may be arranged so that the loops of each coil in the vertex region form a right triangle which matches up with the adjacent coil to form a triangle. FIG. 2F illustrates one variation of this coil arrangement.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

What is claimed is:

1. A Y-shaped Transcranial Magnetic Stimulation (TMS) electromagnet configured to emit a focused magnetic field, the TMS electromagnet comprising:
    a first magnetic coil loop and a second magnetic coil loop arranged about a central axis;
    wherein the first magnetic coil loop is bent relative to the central axis and comprises a plurality of windings and wherein the second magnetic coil loop is bent relative to the central axis and comprises a plurality of windings, the first and second magnetic coil loops meeting at a vertex along the central axis;
    wherein the first magnetic coil loop comprises a first inner coil region at the vertex and the second magnetic coil loop comprises a second inner coil region at the vertex, the plurality of windings within the first inner coil region forming a column that is adjacent and parallel to a second column formed by the plurality of windings within the second inner coil region, the first and second columns aligned along a vertex plane; and
    wherein the first magnetic coil loop further comprises a first outer coil region extending from the vertex and the second magnetic coil loop further comprises a second outer coil region extending from the vertex, and an angle between the first outer coil region and the second outer coil region in the vertex plane is between about 30 degrees and about 120 degrees.

2. The TMS electromagnet of claim 1, wherein the first magnetic coil loop comprise greater than 5 windings.

3. The TMS electromagnet of claim 1, wherein the angle between the first outer coil region and the second outer coil region in the vertex plane is approximately 60 degrees.

4. The TMS electromagnet of claim 1, further comprising a structural support matrix surrounding the first and second magnetic coil loops.

5. The TMS electromagnet of claim 1, wherein the first and second magnetic coil loops are electrically connected so that the current flows from the first magnetic coil loop into the second magnetic coil loop.

6. The TMS electromagnet of claim 1, wherein the vertex is configured so that current will flow in the same direction in the first and second inner coil regions.

7. The TMS electromagnet of claim 1, wherein the first and second magnetic coil loops are arranged symmetrically about the central axis.

8. The TMS electromagnet of claim 1, wherein the first and second magnetic coil loops have approximately the same shape and size.

9. A shaped coil Transcranial Magnetic Stimulation (TMS) electromagnet comprising:
    a first bent magnetic coil loop comprising a first inner coil region and a first outer coil region bent away from the first inner coil region, wherein the first inner coil region comprises a first column formed of a plurality of conductive windings;
    a second bent magnetic coil loop comprising a second inner coil region and a second outer coil region bent away from the second inner coil region, wherein the second inner coil region comprises a second column formed of a plurality of conductive windings; and
    a vertex region connecting the first and second bent magnetic coil loops;
    wherein the vertex region is formed by aligning the first and second columns in parallel; and
    wherein an angle between the first outer coil region and the second outer coil region relative to the vertex region is less than 120 degrees.

10. The shaped TMS electromagnet of claim 9, wherein the vertex region comprise an I-bottomed vertex.

11. The shaped TMS electromagnet of claim 9, wherein the vertex region comprises an interleaved vertex.

12. The shaped TMS electromagnet of claim 9, wherein the first bent magnetic coil loop comprise greater than 5 windings.

13. The shaped TMS electromagnet of claim 9, wherein the angle between the first outer coil region and the second outer coil region relative to the vertex region is approximately 60 degrees.

14. The shaped TMS electromagnet of claim 9, further comprising a structural support matrix surrounding the first and second bent magnetic coil loops.

15. The shaped TMS electromagnet of claim 9, wherein the first and second bent magnetic coil loops are electrically connected so that the current flows from the first bent magnetic coil loop into the second bent magnetic coil loop.

16. The shaped TMS electromagnet of claim 9, wherein the vertex region is configured so that current will flow in the same direction in the portion of the windings forming the first and second columns.

17. The shaped TMS electromagnet of claim 9, wherein the first and second bent magnetic coil loops are arranged symmetrically about the vertex region.

18. The shaped TMS electromagnet of claim 9, wherein the first and second bent magnetic coil loops have approximately the same shape and size.

* * * * *